United States Patent [19]

King et al.

[11] Patent Number: 4,798,829

[45] Date of Patent: Jan. 17, 1989

[54] 1-AZABICYCLO[3,2,2]NONANE DERIVATIVES HAVING 5-HT RECEPTOR ANTAGONIST ACTIVITY

[75] Inventors: Francis D. King; Karen A. Joiner, both of Harlow, England

[73] Assignee: Beecham Group plc., Brentford, Middlesex, England

[21] Appl. No.: 896,664

[22] Filed: Aug. 14, 1986

[30] Foreign Application Priority Data

Aug. 16, 1985 [GB] United Kingdom ............... 8520616

[51] Int. Cl.$^4$ .................. A61K 31/55; C07D 487/08
[52] U.S. Cl. .................................. 514/214; 540/477; 540/478; 540/582
[58] Field of Search ............... 540/477, 582; 514/183, 514/214

[56] References Cited

U.S. PATENT DOCUMENTS 3,405,134 10/1968 Judd .................................. 546/137
4,612,319 9/1986 King .................................. 540/477

FOREIGN PATENT DOCUMENTS 99789 2/1984 European Pat. Off.
158532 10/1985 European Pat. Off.
2125398A 7/1984 United Kingdom.
85-02847 7/1985 World Int. Prop. O.

OTHER PUBLICATIONS

Burger, ed., *Medicinal Chemistry* 2nd ed., Interscience Pub. (1960), p. 42.
Chemical Abstracts, 82, No. 3, p. 416, 15,805h (1975).
Chemical Abstracts, 74, No. 15, 76,304a (1971).
Chemical Abstracts, 62, No. 11, 13,727f (1965).

*Primary Examiner*—Donald G. Daus
*Assistant Examiner*—William A. Teoli, Jr.
*Attorney, Agent, or Firm*—James F. Haley, Jr.; David K. Barr

[57] ABSTRACT

Compounds of formula (I) and pharmaceutically acceptable salts thereof:

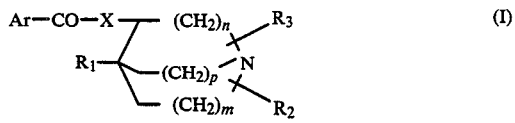

wherein:

n is 1, 2, or 3; and m and p are independently 1 or 2 such that $m+n+p \geq 4$;

X is NH; or O when Ar is of formula (a) and $R_4$ is hydrogen or when Ar is a heteroaromatic group which may be substituted;

$R_1$, $R_2$ and $R_3$ are independently hydrogen, $C_{1-6}$ alkyl, phenyl or phenyl-$C_{1-6}$ alkyl, which phenyl moieties may be substituted by $C_{1-6}$ alkyl, $C_{1-6}$ alkoxy or halogen;

Ar is a group:

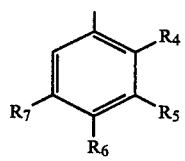

(a)

wherein either $R_4$ is $C_{1-6}$ alkoxy and one of $R_5$, $R_6$, and $R_7$ is hydrogen and the other two are selected from hydrogen, halogen, $CF_3$, $C_{1-6}$ alkylthio, $C_{1-7}$ acyl, $C_{1-10}$ carboxylic acylamino, $C_{1-6}$ alkyl S(O)n wherein n is 0, 1 or 2, nitro or amino, aminocarbonyl or aminosulphonyl optionally substituted by one or two groups selected from $C_{1-6}$ alkyl, $C_{3-8}$ cycloalkyl, $C_{3-8}$ cycloalkyl, $C_{1-4}$ alkyl or phenyl $C_{1-4}$ alkyl groups any of which phenyl moieties may be substituted by one of two groups selected from halogen, $CF_3$, $C_{1-6}$ alkyl or $C_{1-6}$ alkoxy; or $R_4$ is hydrogen and $R_5$, $R_6$ and $R_7$ are independently selected from hydrogen, $C_{1-6}$ alkyl, hydroxy, $C_{1-6}$ alkoxy, $C_{1-6}$ alkylthio or halo; or any two on adjacent carbon atoms together are $C_{1-2}$ alkylenedioxy and the third is hydrogen, $C_{1-6}$ alkyl, $C_{1-6}$ alkoxy or halo;

or Ar is a heteroaromatic group which may be substituted; having gastric motility enhancing activity and/or anti-emetic activity and/or 5-HT antagonist activity, a process for their preparation and their use as pharmaceuticals.

13 Claims, No Drawings

1-AZABICYCLO[3,2,2]NONANE DERIVATIVES HAVING 5-HT RECEPTOR ANTAGONIST ACTIVITY

This invention relates to substituted benzamides and benzoates having pharmacological activity, to a process for their preparation and to their use as pharmaceuticals. EP-A No. 99789 discloses a group of benzamides having a 3-quinuclidinyl side chain and having gastric motility enhancing activity. GB No. 2125398A discloses a group of benzamides and benzoates having a quinuclidinyl side chain and having serotonin M antagonist activity. A structurally distinct group of compounds has now been discovered which compounds have gastric motility enhancing activity and/or anti-emetic activity and/or 5-HT receptor antagonist activity.

Accordingly, the present invention provides a compound of formula (I) or a pharmaceutically acceptable salt thereof:

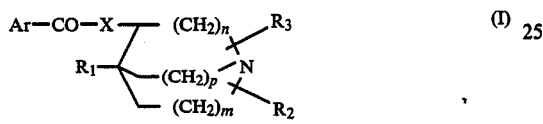

wherein:
n is 1, 2 or 3; and m and p are independently 1 or 2 such that $m+n+p \geq 4$;
H is NH; or O when Ar is of formula (a) and $R_4$ is hydrogen or when Ar is a group of formula (b);
$R_1, R_2$ and $R_3$ are independently hydrogen, $C_{1-6}$ alkyl, phenyl or phenyl-$C_{1-6}$ alkyl, which phenyl moieties may be substituted by $C_{1-6}$ alkyl, $C_{1-6}$ alkoxy or halogen;
Ar is a group of formula (a):

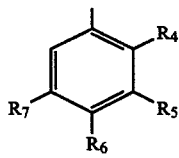

wherein either $R_4$ is $C_{1-6}$ alkoxy and one of $R_5$, $R_6$ and $R_7$ is hydrogen and the other two are selected from hydrogen, halogen, $CF_3$, $C_{1-6}$ alkylthio, $C_{1-7}$ acyl, $C_{1-10}$ carboxylic acylamino, $C_{1-6}$ alkyl S(O)n wherein n is 0, 1 or 2, nitro or amino, aminocarbonyl or aminosulphonyl optionally substituted by one or two groups selected from $C_{1-6}$ alkyl, $C_{3-8}$ cycloalkyl, $C_{3-8}$ cycloalkyl $C_{1-4}$ alkyl or phenyl $C_{1-4}$ alkyl groups any of which phenyl moieties may be substituted by one or two groups selected from halogen, $CF_3$, $C_{1-6}$ alkyl or $C_{1-6}$ alkoxy; or $R_4$ is hydrogen and $R_5$, $R_6$ and $R_7$ are independently selected from hydrogen, $C_{1-6}$ alkyl, hydroxy, $C_{1-6}$ alkoxy, $C_{1-6}$ alkylthio or halo; or any two on adjacent carbon atoms together are $C_{1-2}$ alkylenedioxy and the third is hydrogen, $C_{1-6}$ alkyl, $C_{1-6}$ alkoxy or halo;
or Ar is a group of formula (b):

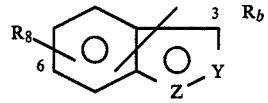

wherein
Z is $CH_2$, O, S or $NR_9$ wherein $R_9$ is hydrogen, $C_{1-6}$ alkyl, $C_{2-7}$ alkenyl, phenyl or phenyl $C_{1-4}$ alkyl either of which phenyl moieties may be substituted by one or two of halogen, $CF_3$, $C_{1-6}$ alkoxy or $C_{1-6}$ alkyl; and Y is CH or N; or Z is CH or N and Y is $NR_a$ or $CHR_a$ where $R_a$ is as defined for $R_9$ above;
$R_b$ is present when the COX linkage is attached at the phenyl ring, and is selected from hydrogen, halogen, $CF_3$, hydroxy, $C_{1-6}$ alkoxy or $C_{1-6}$ alkyl; $R_8$ is hydrogen, $CF_3$, $C_{1-6}$ alkyl, $C_{1-6}$ alkoxy, $C_{1-6}$ alkylthio, $C_{1-7}$ acyl, $C_{1-7}$ acylamino, $C_{1-6}$ alkylsulphonylamino, N-($C_{1-4}$ alkylsulphonyl)-N-$C_{1-4}$ alkylamino, $C_{1-6}$ alkylsulphinyl, hydroxy, nitro or amino, aminocarbonyl, aminosulphonyl, aminosulphonylamino or N-(aminosulphonyl)-$C_{1-4}$ alkylamino optionally N-substituted by one or two groups selected from $C_{1-6}$ alkyl, $C_{3-8}$ cycloalkyl, $C_{3-8}$ cycloalkyl $C_{1-4}$ alkyl, phenyl or phenyl $C_{1-4}$ alkyl groups or optionally N-disubstituted by $C_{4-5}$ polymethylene.

Suitable values for n include 1, 2 or 3, often 2. Preferably n is 2 and m and p are both 1.

X is often NH.

Suitable examples of $R_1$, $R_2$, and $R_3$ include hydrogen, methyl, ethyl, n- and iso-propyl, n-, iso-, sec- and tert-butyl; phenyl, phenylmethyl and phenylethyl, which phenyl moieties may be substituted by one or two methyl, ethyl, n- and iso-propyl, n-, iso-, sec- and tert-butyl; methoxy, ethoxy and n- and iso-propoxy; $CF_3$, fluoro, chloro or bromo.

Often $R_1$, $R_2$ and $R_3$ are hydrogen or methyl, preferably they are all hydrogen.

When Ar is a group of formula (a), examples of $R_4$ when $C_{1-6}$ alkoxy include methoxy, ethoxy and n- and iso-propoxy. Preferably $R_4$ is a methoxy group.

Suitable examples of $R_6$ and $R_7$ then include the following atoms and groups hydrogen; chloro, bromo, $CF_3$, methylthio, ethylthio, n and iso-propylthio; formyl, acetyl, propionyl, n- and iso-butyryl; formylamino, acetylamino, propionylamino, n- and iso-butyrylamino; methyl, ethyl and n- and iso-propylsulphone, -sulphinyl, -thia; nitro; methoxy, ethoxy and n- and iso-propoxy; hydroxy; amino, aminosulphonyl substituted by one or two methyl, ethyl, n- or iso-propyl groups, or by $C_2$, $C_4$ or $C_5$ cycloalkyl or by benzyl optionally substituted as defined above. Particularly suitable $R_6$ and $R_7$ groups include hydrogen, halogen, and amino; and as "intermediates", acylamino and nitro, which can conveniently be converted to the corresponding amino groups.

Particularly preferred $R_6$ groups include 4-amino and 4-acylamino. Most preferably $R_6$ is 4-amino. Particularly preferred $R_7$ groups include 5-halo, such as 5-chloro.

In another group of compounds $R_6$ is hydrogen, 4-halo (e.g. chloro), or amino; and $R_7$ is 5-$C_{1-6}$ alkyl S(O)n (such as 5-methylsulphonyl, -sulphinyl or -thia) or 5-optionally alkylated aminosulphonyl.

When $R_4$ is hydrogen, examples of $R_5$ include halo, such as chloro and $C_{1-6}$ alkoxy, such as methoxy. Preferably $R_5$ is chloro.

Examples of $R_6$ then include hydrogen, halo, such as chloro, hydroxy and $C_{1-6}$ alkoxy such as methoxy. Preferably $R_6$ is hydrogen or chloro.

Examples or $R_7$ then include hydrogen, halo such as chloro and $C_{1-6}$ alkoxy, such as methoxy. Preferably $R_7$ is hydrogen or chloro.

Z is often $NR_9$ and Y is CH or N; or Z is N and $R_a$ is as defined for $R_9$.

Suitable values for $R_9$ or $R_a$ include hydrogen, methyl, ethyl, n- and iso-propyl; vinyl, prop-1-enyl, prop-2-enyl, 1-methylvinyl, but-1-enyl, but-2-enyl, but-3-enyl, 1-methylenepropyl, 1-methylprop-1-enyl and 1-methylprop-2-yl in their E and Z forms where stereoisomerism exists, phenyl and benzyl optionally substituted by one or two of chloro, bromo, $CF_3$, methoxy, ethoxy, n- and iso-propoxy, methyl, ethyl, n- and iso-propyl. Often $R_9/R_a$ is hydrogen, methyl or ethyl.

Suitable values for $R_b$ when present include hydrogen, chloro, bromo, $CF_3$, methoxy, ethoxy, n- and iso-propoxy, methyl, ethyl, n- and iso-propyl.

Often the -COX- linkage is attached at positions 3 or 6, as depicted in formula (b).

The pharmaceutically acceptable salts of the compounds of the formula (I) include acid addition salts with conventional acids such as hydrochloric, hydrobromic, boric, phosphoric, sulphuric acids and pharmaceutically acceptable organic acids such as acetic, tartaric, maleic, citric, succinic, benzoic, ascorbic, methanesulphonic, α-keto glutaric, α-glycerophosphoric, and glucose-1-phosphoric acids.

The pharmaceutically acceptable salts of the compounds of the formula (I) are usually acid addition salts with acids such as hydrochloric, hydrobromic phosphoric, sulphuric, citric, tartaric, lactic and acetic acid. Preferably the acid addition salt is the hydrochloride salt.

Examples of pharmaceutically acceptable salts include quaternary derivatives of the compounds of formula (I) quaternised by compounds such as $R_{10}$-T wherein $R_{10}$ is $C_{1-6}$ alkyl, phenyl-$C_{1-6}$ alkyl or $C_{5-7}$ cycloalkyl, and T is a radical corresponding to an anion of an acid. Suitable examples of $R_{10}$ include methyl, ethyl and n- and iso-propyl; and benzyl and phenethyl. Suitable examples of T include halide such as chloride, bromide and iodide.

Examples of pharmaceutically acceptable salts of the compounds of formula (I) also include internal salts such as pharmaceutically acceptable N-oxides.

The compounds of the formula (I), their pharmaceutically acceptable salts, (including quaternary derivatives and N-oxides) may also form pharmaceutically acceptable solvates, such as hydrates, and these are included whenever a compound of formula (I) or a salt thereof is herein referred to.

It will of course be realised that some of the compounds of the formula (I) have chiral or prochiral centres and thus are capable of existing in a number of stereoisomeric forms including enantiomers. The invention extends to each of these stereoisomeric forms (including enantiomers), and to mixtures thereof (including racemates). The different stereoisomeric forms may be separated one from the other by the usual methods.

It will also be realised that compounds of the formula (I) wherein $R_9$ is hydrogen can exist as two tautomeric forms i.e. that wherein $R_9$ is hydrogen and Y is CH or N and that wherein $R_a$ is hydrogen and Z is N. The invention extends to each of these forms and to mixtures thereof. The predominant tautomeric form is usually that wherein $R_9$ is hydrogen.

A group of compound within formula (I) is of formula (II):

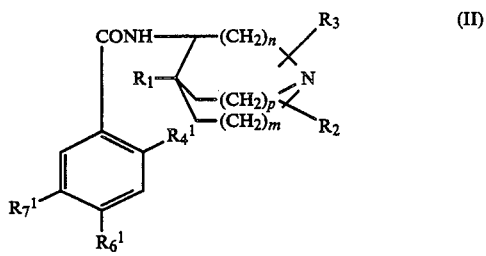

wherein
$R_4^1$ is $C_{1-6}$ alkoxy;
$R_6^1$ is amino or $C_{1-7}$ alkanoylamino;
$R_7^1$ is halo or $C_{1-6}$ alkylthio;
and the remaining variables are as defined in formula (I). Suitable examples and preferred values for the variables are as described for the corresponding variables under formula (I).

There is a further group of compounds within formula (I) of formula (III):

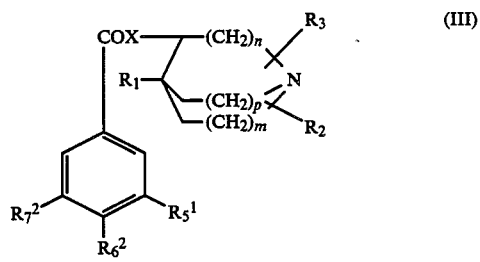

wherein
$R_5^1$ is halo, $C_{1-6}$ alkoxy or $C_{1-6}$ alkyl;
$R_6^2$ is hydrogen or $C_{1-6}$ alkoxy;
$R_7^2$ is halo, $C_{1-6}$ alkoxy or $C_{1-6}$ alkyl; and the remaining variables are as defined in formula (I).

Suitable examples and preferred values for the variables are as described for the corresponding variables under formula (I).

There is another group of compounds within formula (I) of formula (IV):

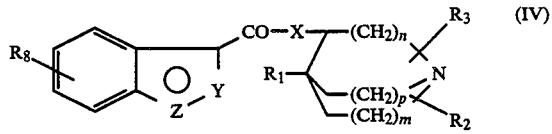

wherein the variables are as defined in formula (I).

Suitable examples and preferred values for the varibles are as described for the corresponding variables under formula (I).

The invention also provides a process for the preparation of a compound of formula (I) or a pharmaceutically acceptable salt thereof, which process comprises reacting a compound of formula (V):

Ar G      (V)

with a compound of formula (VI):

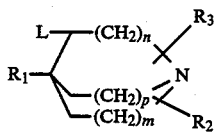

wherein G is COQ where Q is a leaving group; and L is NH₂ or OH or a reactive derivative thereof and the remaining variables are as hereinbefore defined; and thereafter optionally converting any $R_4$, $R_5$, $R_6$, $R_7$, $R_8$, $R_a$ and $R_b$ group to another $R_4$, $R_5$, $R_6$, $R_7$, $R_8$, $R_a$ and $R_b$ group respectively, and optionally forming a pharmaceutically acceptable salt of the resultant compound of formula (I).

Examples of leaving groups Q, displaceable by a nucleophile, include halogen such as chloro and bromo, hydroxy, carboxylic acyloxy such as $C_{1-4}$ alkanoyloxy or $C_{1-4}$ alkoxycarbonyloxy and activated hydrocarbyloxy such as pentachlorophenoxy.

Alternatively, when G is COQ, Ar is of formula (b) and Z is NH in formula (V), a nitrogen heterocycle may act as the leaving group i.e. that obtained by reaction of a compound of formula (V) wherein G is CO₂H and Z is NH with thionyl chloride to give a diindazolo[2,3-a,2′,3′-d]pyrazine-7,14-dione.

If a group Q is a halide, then the reaction is preferably carried out at non-extreme temperatures in an inert non-hydroxylic solvent, such as benzene, dichloromethane, toluene, diethyl ether, THF (tetrahydrofuran) or DMF (dimethylformamide). It is also preferably carried out in the presence of an acid acceptor, such as an organic base, in particular a tertiary amine, such as triethylamine, trimethylamine, pyridine or picoline, some of which can also function as the solvent. Alternatively, the acid acceptor can be inorganic, such as calcium carbonate, sodium carbonate or potassium carbonate. Temperatures of 0°–100° C., in particular 10°–80° C. are suitable.

If a group Q is hydroxy, then the reaction is generally carried out in an inert non-hydroxylic solvent, such as dichloromethane, THF or DMF optionally in the presence of a dehydrating catalyst, such as a carbodiimide, for example dicyclohexylcarbodiimide. The reaction may be carried out at any non-extreme temperature, such as $-10°$ to 100° C., for example, 0° to 80° C. Generally, higher reaction temperatures are employed with less active compounds whereas lower temperatures are employed with the more active compounds.

If a group Q is carboxylic acyloxy, then the reaction is preferably carried in substantially the same manner as the reaction when Q is halide. Suitable examples of acyloxy leaving groups include $C_{1-4}$ alkanoyloxy and $C_{1-4}$ alkoxycarbonyloxy, in which case the reaction is preferably carried out in an inert solvent, such as dichloromethane, at a non-extreme temperature for example ambient temperatures in the presence of an acid acceptor, such as triethylamine. $C_{1-4}$ alkoxycarbonyloxy leaving groups may be generated in situ by treatment of the corresponding compound wherein Q is hydroxy with a $C_{1-4}$ alkyl chloroformate.

If a group Q is activated hydrocarbyloxy then the reaction is preferably carried out in an inert polar solvent, such as dimethylformamide. It is also preferred that the activated hydrocarbyloxy group is a pentachlorophenyl ester and that the reaction is carried out at ambient temperature.

When the leaving group Q is a nitrogen heterocycle as hereinbefore described the reaction is carried out in a similar manner as when Q is a halide. When L is OH or a reactive derivative thereof, the reactive derivative is often a salt, such as the sodium or lithium salt.

Pharmaceutically acceptable salts of the compounds of this invention may be formed conventionally.

The salts may be formed for example by reaction of the base compound of formula (I) with a pharmaceutically acceptable organic or inorganic acid.

It will be apparent that compounds of the formula (I) containing an $R_4$, $R_5$, $R_6$, $R_7$, $R_8$, $R_a$ or $R_b$ group which is convertible to another $R_4$, $R_5$, $R_6$, $R_7$, $R_8$, $R_a$ or $R_b$ group are useful novel intermediates. A number of such conversions is possible not only for the end compounds of formula (I), but also for their intermediates as follows:

(i) a hydrogen substituent is convertible to a nitro substituent by nitration;
(ii) a nitro substituent is convertible to an amino substituent by reduction;
(iii) a $C_{1-7}$ acylamino substituent is convertible to an amino substituent by deacylation;
(iv) an amino substituent is convertible to a $C_{1-4}$ acylamino substituent by acylation with a carboxylic acid derivative;
(v) a hydrogen substituent is convertible to a halogen substituent by halogenation;
(vi) a $C_{1-6}$ alkylthio or $C_{1-6}$ alkylsulphinyl substituent is convertible to a $C_{1-6}$ alkylsulphinyl or a $C_{1-6}$ alkylsulphonyl substituent respectively by oxidation;
(vii) an amino, aminocarbonyl, aminosulphonyl, aminosulphonylamino or N-(aminosulphonyl)-N-$C_{1-4}$ alkylamino substituent is convertible to a corresponding substituent substituted by one or two groups selected from $C_{1-6}$ alkyl, $C_{3-8}$ cycloalkyl, $C_{1-4}$ alkyl or phenyl $C_{1-4}$ alkyl groups any of which phenyl groups may be substituted by one or more groups selected from halogen, trifluoromethyl, $C_{1-6}$ alkyl, $C_{1-6}$ alkoxy and nitro, or disubstituted by $C_{4-5}$ polymethylene , by N-alkylation;
(viii) an amino substituent is convertible to a $C_{1-6}$ alkylsulphonylamino group or an aminosulphonylamino group optionally N-substituted as defined by acylation with a $C_{1-6}$ alkylsulphonic acid or di-substituted amisosulphonyl chloride.
(ix) A $C_{1-4}$ alkylamino substituent group is convertible to a N-($C_{1-6}$ alkylsulphonyl)N-$C_{1-4}$ alkylamino group or an N-(amino sulphonyl)N-$C_{1-4}$ alkylamino group optionally N-substituted as defined by acylation with a $C_{1-6}$ alkylsulphonic acid or di-substituted amisosulphonyl chloride.

Conversions (i) to (ix) are only exemplary and are not exhaustive of the possibilities.

In regard to (i), nitration is carried out in accordance with known procedures.

In regard to (ii), the reduction is carried out with a reagent suitable for reducing nitroanisole to aminoanisole.

In regard to (iii), deacylation is carried out by treatment with a base, such as an alkali metal hydroxide.

In regard to (iv), (viii), and (ix) the acylation is carried out with an acylating agent, such as the corresponding acid or acid chloride. Formylation is carried out with the free acid.

In regard to (v), halogenation is carried out with conventional halogenating agents.

In regard to (vi), oxidation is carried out at below ambient temperatures in a non-aqueous solvent, such as a chlorinated hydrocarbon, in the presence of an organic peracid, such as 3-chloroperbenzoic acid, or in water in the presence of a soluble strong inorganic oxidant, such as an alkali metal permanganate or in aqueous hydrogen peroxide. It will be realised that this process may also N-oxidise the

moiety and suitable precautions will routinely be taken by the skilled man.

In regard to (vii), alkylation is carried out with a corresponding alkylating agent such as the chloride or bromide under conventional conditions.

Before carrying out any of these conversions, the effect, if any, on other substituents should be considered, and such reagents as are appropriate should be selected together with the adoption of such precautionary measures as are necessary. For example, O-alkylation and O-acylation may also produce N-alkylated and N-acylated products respectively unless the nitrogen atom(s) is (are) previously protected. This may be conveniently achieved by carrying out the alkylation or acylation reaction in a strong acid, such as trifluoroacetic acid, which protonates, and thereby protects, the nitrogen atom(s).

The compounds of formula (V) are known or are preparable analogously to, or routinely from, known compounds.

Compounds of formula (VI) are novel and form an aspect of the present invention. They may be prepared from the corresponding ketones in accordance with the processes described in the descriptions hereinafter or by analogous methods thereto.

Compounds of formula (VI) wherein L is NH$_2$ may be prepared from the corresponding ketone by reaction with hydroxylamine to form the oxime which then may be reduced conventionally using AlH$_3$ or sodium/amyl alcohol.

Compounds of formula (VI) wherein L is OH may be prepared by reduction of the corresponding ketone by conventional methods such as lithium aluminium hydride reduction.

The ketones (of formula (VII)) may be prepared by methods analogous to those known in the art such as Dieckmann or Thorpe cyclisation or ring expansion methods as follows:

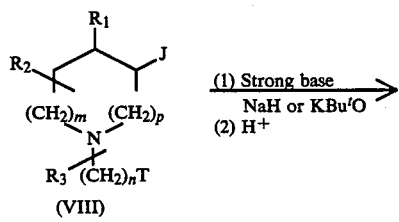

(VIII)

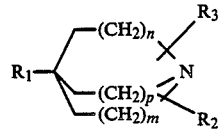

(VII)

wherein J and T in formula (VIII) are independently cyano groups or C$_{1-4}$ alkyl ester groups.

The compounds of the present invention have gastric motility enhancing activity and/or anti-emetic activity and/or 5-HT antagonist activity. Compounds having gastric motility enhancing activity are useful in the treatment of disorders such as retarded gastric emptying, dyspepsia, flatulence, oesophagal reflux and peptic ulcer. Compounds having 5-HT antagonist activity are useful in the treatment of migraine, cluster headaches, trigeminal neuralgia and/or cytotoxic agent or radiation induced nausea and vomiting. Examples of cytotoxic agents include cisplatin, doxorubicin and cyclophosphamide. Compounds which are 5-HT antagonists may also be of potential use in the treatment of CNS disorders such as anxiety and psychosis; arrhythmia, obesity and irritable bowel syndrome.

The compounds of formula (I) of particular interest for their 5-HT antagonist activity are the compounds of formula (I) wherein Ar is of formula (a) and R$_4$ is hydrogen, or Ar is of formula (b). The compounds of formula (I) of particular interest for their gastric motility enhancing activity and anti-emetic activity are the compounds of formula (I) where Ar is of formula (a) and R$_4$ is C$_{1-6}$ alkoxy.

The invention also provides a pharmaceutical composition comprising a compound of formula (I), or a pharmaceutically acceptable salt thereof, and a pharmaceutically acceptable carrier.

Such compositions are prepared by admixture and are suitably adapted for oral or parenteral administration, and as such may be in the form of tablets, capsules, oral liquid preparations, powders, granules, lozenges, reconstitutable powders, injectable and infusable solutions or suspensions or suppositories. Orally administrable compositions are preferred, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art, for example with an enteric coating.

Suitable fillers for use include cellulose, mannitol, lactose and other similar agents. Suitable disintegrants include starch, polyvinylpolypyrrolidone and starch derivatives such as sodium starch glycollate. Suitable lubricants include, for example, magnesium stearate. Suitable pharmaceutically acceptable wetting agents include sodium lauryl sulphate. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

Oral liquid preparations are usually in the form of aqueous or oily suspensions, solutions, emulsions, syrups, or elixirs or are presented as a dry product for reconstitution with water or other suitable vehicle before use. Such liquid preparations may contain conventional additives such as suspending agents, emulsifying agents, non-aqueous vehicles (which may include edible oils), preservatives, and flavouring or colouring agents. The oral compositions may be prepared by conventional methods of blending, filling or tabletting. Repeated blending operations may be used to distribute the active agent throughout those compositions employing large quantities of fillers. Such operations are, of course, conventional in the art. For parenteral administration, fluid unit dose forms are prepared containing a compound of the present invention and a sterile vehicle. The compound, depending on the vehicle and the concentration, can be either suspended or dissolved. Parenteral solutions are normally prepared by dissolving the compound in a vehicle and filter sterilising before filling into a suitable vial or ampoule and sealing.

Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure of ethylene oxide before suspending in the sterile vehicle. Advantageously, a surfactant or wetting agent is included in the composition to facilitate uniform distribution of the compound of the invention. The invention further provides a method of treatment or prophylaxis of disorders relating to impaired gastrointestinal motility and/or emesis and/or migraine, cluster headaches, trigeminal neuralgia and/or cytotoxic agent or radiation induced vomiting in mammals, such as humans, which comprises the administration of an effective amount of a compound of the formula (I) or a pharmaceutically acceptable salt thereof.

An amount effective to treat the disorders hereinbefore described depends on the relative efficacies of the compounds of the invention, the nature and severity of the disorder being treated and the weight of the mammal. However, a unit dose for a 70 kg adult will normally contain 0.5 to 1000 mg for example 1 to 500 mg, of the compound of the invention. Unit doses may be administered once or more than once a day, for example, 2, 3 or 4 times a day, more usually 1 to 3 times a day, that is in the range of approximately 0.001 to 50 mg/kg/day, more usually 0.002 to 25 mg/kg/day.

No adverse toxicological effects are indicated at any of the aforementioned dosage ranges.

The invention also provides a compound of formula (I) or a pharmaceutically acceptable salt thereof for use as an active therapeutic substance, in particular for use in the treatment of disorders relating to impaired gastrointestinal motility and/or emesis and/or migraine, cluster headaches, trigeminal neuralgia and/or cytotoxic agent or radiation induced vomiting.

The following Examples illustrate the preparation of compounds of formula (I); the following Descriptions illustrate the preparation of intermediates.

Description 1

1-Azabicyclo[3.2.2.]nonan-4-one oxime hydrochloride

D1)

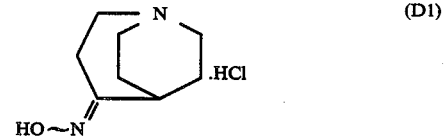

Hydroxylamine hydrochloride (2.1 g) was added to a solution of 1-azabicyclo[3.2.2.]nonan-4-one (2.77 g) in ethanol (30 ml) and the mixture was heated under reflux for 2 h. On cooling the reaction mixture to room temperature, the white solid was collected by filtration and dried in vacuo to give the title compound (2.84 g, 75%).

$^1$H-NMR (DMSO-$d_6$): δ11.65 (brs. 1H), 10.75,10.65 (2s, 1H), 3.70–2.40 (m, 9H), 2.35–1.50 (m, 4H).

Description 2

4-Amino-1-azabicyclo[3.2.2]nonane (D2)

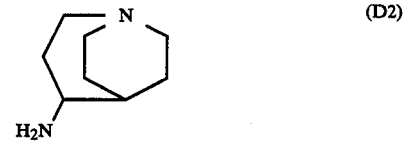

Sodium (5.6 g) was added portionwise to a suspension of 1-azabicyclo[3.2.2]nonan-4-one oxime hydrochloride (D1) (2.8 g) in amyl alcohol (100 ml) which was heated under reflux. After all the sodium had reacted, the mixture was cooled to 50° and water (20 ml) was added carefully. The aqueous phase was separated and the amyl alcohol was extracted with 5N hydrochloric acid (2×15 ml). The combined acid extract was washed with diethyl ether and the solvent evaporated in vacuo to give 4-amino-1-azabicyclo[3.2.2]nonane hydrochloride. The hydrochloride salt was basified with 40% sodium hydroxide and the aqueous phase was saturated with potassium carbonate, extracted with diethyl ether, dried (Na$_2$SO$_4$) and the solvent evaporated in vacuo to give the title compound (1.4 g, 68%).

EXAMPLE 1

(±) 4-Acetamido-5-chloro-2-methoxy-N-[4'-(1'-azabicyclo[3.2.2]nonyl)]benzamide (E1)

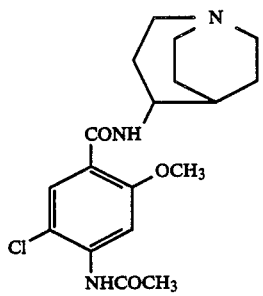

To 4-acetamido-5-chloro-2-methoxybenzoyl chloride (1.96 g) in dry dichloromethane (75 ml) and triethylamine (0.89 ml) at 0° was added the crude 4-amino-1-azabicyclo[3.2.2]nonane (D2) (0.9 g) in dry dichloromethane (20ml). The reaction mixture was stirred at room temperature for 2h, then treated with 2.5N sodium hydroxide solution (10 ml). The organic phase was separated, dried ($Na_2SO_4$) and the solvent evaporated in vacuo to give the title compound (E1) (2.15 g, 92%) as a white foam.

$^1$H-NMR (CDCl$_3$): δ=8.25 (s, 1H), 8.15 (s, 1H), 7.85 (m, 2H), 4.45–3.80 (m, 1H), 3.90 (s, 3H), 3.40–2.40 (m, 6H), 2.40–1.10 (m, 7H) 2.25 (s, 3H).

EXAMPLE 2

(±) 4-Amino-5-chloro-2-methoxy-N-[4'-(1'-azabicylo[3.2.2]nonyl)]benzamide (E2)

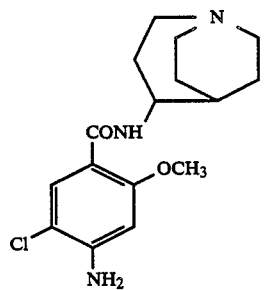

(±) 4-Acetamido-5-chloro-2-methoxy-N-[4'-(1'-azabicyclo[3.2.2]nonyl)]benzamide (2.15 g) was heated under reflux in ethanol (40 ml) and 2.5 N sodium hydroxide solution (4.7 ml) for 2h. After concentration in vacuo, the aqueous residue was extracted with dichloromethane (2×100 ml). The organic phase was dried ($Na_2SO_4$), concentrated and the residue purified by column chromatography on alumina, eluting with CHCl$_3$ to give the title compound (E2) (0.58 g, 31%) m.p. 168°–72°.

$^1$H-NMR (CDCl$_3$): δ8.10 (s, 1H), 7.90–7.65 (m, 1H), 6.30 (s, 1H), 4.65–3.70 (m, 3H), 3.90 (s, 3H), 3.40–2.60 (m, 6H), 2.30–1.30 (m, 7H).

EXAMPLE 3

(±) 3,5-Dichloro-N-[4'-(1'-azabicyclo[3.2.2]nonyl)]benzamide (E3)

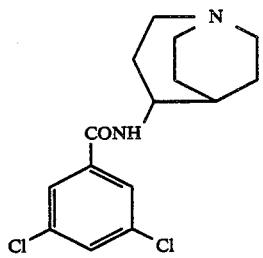

Following the procedure outlined in Example 1, reaction of 4-amino-1-azabicyclo[3.2.2]nonane (D2) (0.25 g) with 3,5-dichlorobenzoyl chloride (0.45 g) afforded (±) 3,5-dichloro-N-[4'-(1'-azabicyclo[3.2.2]nonyl)]benzamide (E3) (0.35g, 63%) m.p. 169°–70°

$^1$H-NMR (CDCl$_3$): δ7.60 (d, 2H), 7.48 (m, 1H), 6.25 (bd, 1H), 4.21 (quin, 1H), 3.34–3.20 (m, 1H), 3.18–2.77 (m, 5H), 2.18–1.54 (m, 7H).

EXAMPLE 4

(±) 1-Methylindazol-3-yl-N-[4'-(1'-azabicylo[3.2.2]nonyl)]carboxamide (E4)

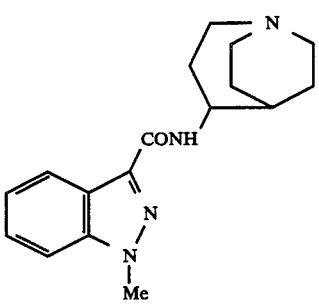

Following the procedure outlined in Example 1, reaction of 4-amino-1-azabicyclo[3.2.2]nonane (D2) (0.1 g) with 1-methyl-3-indazoloyl chloride (0.17 g) afforded (±) 1-methylindazol-3-yl-N-(4'-(1'-azabicyclo[3.2.2]nonyl)]carboxamide (E4) (0.065 g, 31%) m.p. 117°–8°

$^1$H-NMR (CDCl$_3$): δ8.35 (m, 1H), 7.50–7.25 (m, 3H), 7.05 (bd, 1H), 4.39–4.27 (m, 1H), 4.10 (s, 3H), 3.40–2.84 (m, 6H), 2.31–1.57 (m, 7H).

Pharmacology

Antagonism of the von Bezold-Jarisch reflex

The compounds were evaluated for antagonism of the von Bezold-Jarisch reflex evoked by 5-HT in the anaesthetised rat according to the following method:

Male rats 250–350 g, were anaesthetised with urethane (1.25 g/kg intraperitoneally) and blood pressure and heart rate recorded as described by Fozard J. R. et al., J. Cardiovasc. Pharmacol. 2, 229–245 (1980). A submaximal dose of 5-HT (usually 6 μg/kg) was given repeatedly by the intravenous route and changes in heart rate quantified. Compounds were given intravenously and the concentration required to reduce the 5-HT-evoked response to 50% of the control response (ED$_{50}$) was then determined.

The compound of Example 3 had an ED$_{50}$ of 0.008 mg/kg i.v.

We claim:

1. A compound of frmula (I) or a pharmaceutically acceptable salt thereof:

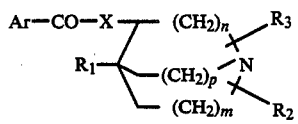

(I)

wherein:

n is 2 and m and p are both 1

X is NH; or O when Ar is of formula (a) and R$_4$ is hydrogen or when Ar is a group of formula (b);

R$_1$, R$_2$ and R$_3$ are independently hydrogen, C$_{1-6}$ alkyl, phenyl or phenyl-C$_{1-6}$ alkyl, which phenyl moieties may be substituted by C$_{1-6}$ alkyl, C$_{1-6}$ alkoxy or halogen;

Ar is a group of formula (a):

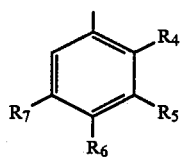

(a)

wherein either R$_4$ is C$_{1-6}$ alkoxy and one of R$_5$, R$_6$ and R$_7$ is hydrogen and the other two are selected from hydrogen, halogen, CF$_3$, C$_{1-6}$ alkylthio, C$_{1-7}$ acyl, C$_{1-10}$ carboxylic acylamino, C$_{1-6}$ alkyl S(O)n wherein n is 0, 1 or 2, nitro or amino, aminocarbonyl or aminosulphonyl optionally substituted by one or two groups selected from C$_{1-6}$ alkyl, C$_{3-8}$ cycloalkyl, C$_{3-8}$ cycloalkyl C$_{1-4}$ alkyl or phenyl C$_{1-4}$ alkyl groups any of which phenyl moieties may be substituted by one or two groups selected from halogen, CF$_3$, C$_{1-6}$ alkyl or C$_{1-6}$ alkoxy; or R$_4$ is hydrogen and R$_5$, R$_6$ and R$_7$ are independently selected from hydrogen, C$_{1-6}$ alkyl, C$_{1-6}$ alkoxy, C$_{1-6}$ alkylthio or halo; or any two on adjacent carbon atoms together are C$_{1-2}$ alkylenedioxy and the third is hydrogen, C$_{1-6}$ alkyl, C$_{1-6}$ alkoxy or halo;

or Ar is a group of formula (b):

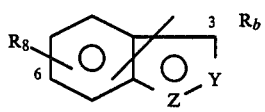

(b)

wherein

Z is CH$_2$, O, S or NR$_9$ wherein R$_9$ is hydrogen, C$_{1-6}$ alkyl, C$_{2-7}$ alkenyl, phenyl or phenyl C$_{1-4}$ alkyl either of which phenyl moieties may be substituted by one or two of halogen, CF$_3$, C$_{1-6}$ alkoxy or C$_{1-6}$ alkyl; and Y is CH or N; or Z is CH or N and Y is NR$_a$ or CHR$_a$ where R$_a$ is as defined for R$_9$ above;

R$_b$ is present when the COX linkage is attached at the phenyl ring, and is selected from hydrogen, halogen, CF$_3$, hydroxy, C$_{1-6}$ alkoxy or C$_{1-6}$ alkyl; R$_8$ is hydrogen, CF$_3$, C$_{1-6}$ alkyl, C$_{1-6}$ alkoxy, C$_{1-6}$ alkylthio, C$_{1-7}$ acyl, C$_{1-7}$ acylamino, C$_{1-6}$ alkylsulphonylamino, N-(C$_{1-6}$ alkylsulphonyl)-N-C$_{1-4}$ al- kylamino, C$_{1-6}$ alkylsulphinyl, hydroxy, nitro or amino, aminocarbonyl, aminosulphonyl, aminosulphonylamino or N-(aminosulphonyl)-C$_{1-4}$ alkylamino optionally N-substituted by one or two groups selected from C$_{1-6}$ alkyl, C$_{3-8}$ cycloalkyl, C$_{3-8}$ cycloalkyl C$_{1-4}$ alkyl, phenyl or phenyl C$_{1-4}$ alkenyl groups or optionally N-disubstituted by C$_{4-5}$ polymethylene.

2. A compound according to claim 1 of formula (II):

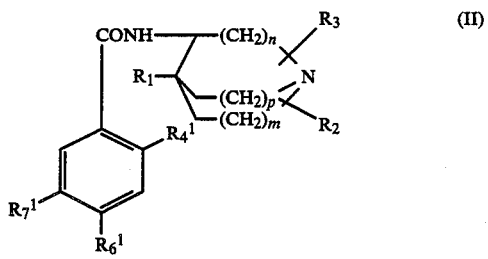

(II)

wherein

R$_4^1$ is C$_{1-6}$ alkoxy;

R$_6^1$ is amino or C$_{1-7}$ alkanoylamino;

R$_7^1$ is halo or C$_{1-6}$ alkylthio; and the remaining variables are as defined in claim 1.

3. A compound according to claim 2 wherein R$_4^1$ is methoxy, R$_6^1$ is amino and R$_7^1$ is chloro or bromo.

4. A compound according to claim 1 of formula (III):

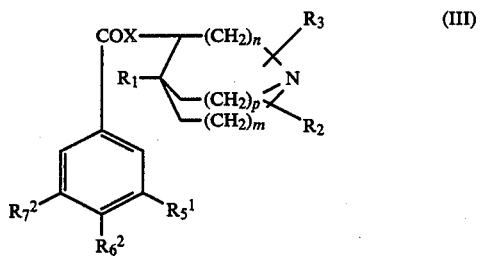

(III)

wherein

R$_5^1$ is halo, C$_{1-6}$ alkoxy or C$_{1-6}$ alkyl;

R$_6^2$ is hydrogen or C$_{1-6}$ alkoxy;

R$_7^2$ is halo, C$_{1-6}$ alkoxy or C$_{1-6}$ alkyl; and the remaining variables are as defined in claim 1.

5. A compound according to claim 3 wherein R$_5^1$ and R$_7^2$ are both chloro or both methyl and R$_6^2$ is hydrogen.

6. A compound according to claim 1 of formula (IV):

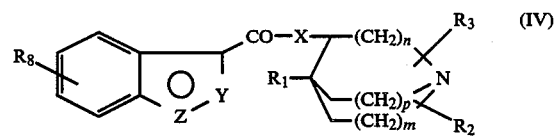

(IV)

wherein the variables are as defined is claim 1.

7. A compound according to claim 6 wherein Y is N and Z is NR$_9$ as defined in claim 1.

8. A compound according to claim 1 wherein R$_1$, R$_2$ and R$_3$ are all hydrogen, m is 1, n is 2 and p is 1.

9. 4-Amino-5-chloro-2-methoxy-N-[4'-(1'-azabicylo [3.2.2]nonyl)]benzamide or a pharmaceutically acceptable salt thereof.

10. 3,5-Dichloro-N-[4'-(1'-azabicyclo[3.2.2]nonyl)]benzamide or a pharmaceutially acceptable salt thereof.

11. 1-Methylindazol-3-yl-N-[4'-(1'-azabicyclo[3.2.2]nonyl)]carboxamide or a pharmaceutically acceptable salt thereof.

12. A pharmaceutical composition for the treatment of disorders relating to impaired gastro-intestinal motility; emesis; migraine, or cluster headaches comprising an effective amount of a compound according to claim 1, and a pharmaceutically acceptable carrier.

13. A method for the treatment of disorders relating to impaired gastro-intestinal motility, or emesis; migraine, or cluster headaches in mammals which comprises the administration of an effective amount of a compound according to claim 1.

* * * * *